(12) United States Patent
Koguchi et al.

(10) Patent No.: US 7,411,089 B2
(45) Date of Patent: Aug. 12, 2008

(54) NATEGLINIDE CRYSTALS

(75) Inventors: Yoshihito Koguchi, Kawasaki (JP); Tomoko Nakao, Kawasaki (JP); Michito Sumikawa, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 211 days.

(21) Appl. No.: 10/965,171

(22) Filed: Oct. 15, 2004

(65) Prior Publication Data

US 2005/0101672 A1    May 12, 2005

Related U.S. Application Data

(63) Continuation of application No. PCT/JP03/04686, filed on Apr. 14, 2003.

(30) Foreign Application Priority Data

Apr. 15, 2002    (JP)    ............... 2002-111963

(51) Int. Cl.
*C07C 229/00*    (2006.01)
*C07C 51/15*    (2006.01)

(52) U.S. Cl. ..................... 562/445; 562/554

(58) Field of Classification Search ................. 562/433, 562/442, 444, 445
See application file for complete search history.

(56) References Cited

U.S. PATENT DOCUMENTS

| | | | |
|---|---|---|---|
| 5,463,116 A * | 10/1995 | Sumikawa et al. | .......... 562/450 |
| 5,488,150 A | 1/1996 | Sumikawa et al. | |
| 6,861,553 B2 * | 3/2005 | Yahalomi et al. | ........... 562/450 |
| 2003/0229249 A1 | 12/2003 | Sumikawa et al. | |
| 2005/0101672 A1 | 5/2005 | Koguchi et al. | |

FOREIGN PATENT DOCUMENTS

| | | |
|---|---|---|
| CA | 2 425 538 A1 | 4/2003 |
| EP | 0 196 222 A2 | 10/1986 |
| JP | 5-208943 | 2/1993 |
| WO | WO 02/34713 A1 | 5/2002 |

OTHER PUBLICATIONS

U.S. Appl. No. 11/757,769, filed Jun. 4, 2007, Sumikawa, et al.

* cited by examiner

*Primary Examiner*—Karl Puttlitz
(74) *Attorney, Agent, or Firm*—Oblon, Spivak, McClelland, Maier & Neustadt, P.C.

(57) ABSTRACT

New nateglinide crystals, i.e. nateglinide A-type crystals (main peaks in powder X-ray diffraction: 4.4°, 5.2°, 15.7°, 18.5°(2θ)), M-type crystals (main peaks in powder X-ray diffraction: 6.0°, 14.2°, 15.2°, 18.8°(2θ)) and P-type crystals (main peaks in powder X-ray diffraction: 4.8°, 5.3°, 14.3°, 15.2°(2θ)), can be produced by dissolving nateglinide in a solvent in which nateglinide is highly soluble and then adding a solvent in which nateglinide is difficultly soluble or, alternatively, by dissolving nateglinide in a mixed solvent composed of a solvent in which nateglinide is highly soluble and another solvent in which it is difficultly soluble, cooling the nateglinide solution to form crystals, filtering the mixture and drying the crystals at a specified temperature.

15 Claims, 3 Drawing Sheets

NATEGLINIDE CRYSTALS

CROSS-REFERENCE TO A RELATED APPLICATION

The present application is a continuation of International Application PCT/JP03/04686, filed on Apr. 14, 2003, which claims priority to Japanese Patent Application No. JP 2002-111963, filed on Apr. 15, 2002.

BACKGROUND OF THE INVENTION

The present invention relates to new crystals of nateglinide (the chemical name: N-(trans-4-isopropylcyclohexylcarbonyl)-D-phenylalanine) and methods for producing nateglinide B-type crystals from them. More specifically, the present invention relates to nateglinide A-type crystals, M-type crystals and P-type crystals, methods for producing them and methods for producing nateglinide B-type crystals from those crystals.

Nateglinide represented by general formula 1 given below is used as a therapeutic agent for diabetes in Japan and also in Western countries because it effectively lowers blood glucose. This compound is described in Japanese Patent Publication No. Hei 4-15221. According to this publication and Japanese Patent No. 2,508,949, it is known that this compound has B-type and H-type crystals. It was confirmed that B-type crystals are obtained by, for example, crystallizing them from methanol/water and then drying them under heating and that the melting point of the crystals is 129-130° C. On the other hand, nateglinide H-type crystals are described in Japanese Patent No. 2,508,949 and the melting point thereof is confirmed to be 136 to 142° C.

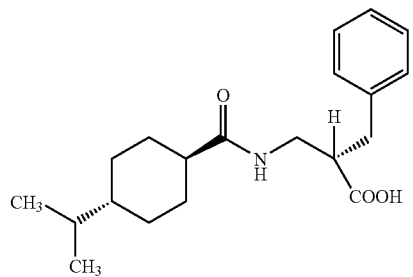

DISCLOSURE OF THE INVENTION

An object of the present invention is to provide useful, new crystal forms of nateglinide other than B-type and H-type crystals thereof.

Another object of the present invention is to provide efficient methods for producing nateglinide in these crystal forms.

After intensive investigations on nateglinide crystals, the inventors have found new useful crystal forms (hereinafter referred to as A-type crystals, M-type crystals and P-type crystals) different from B-type crystals or H-type crystals. The inventors have also found that crystals of these types can be converted into B-type crystals by treating them under specified conditions. The present invention has been completed on the basis of this finding.

That is, the present invention provides new nateglinide A-type crystals, M-type crystals and P-type crystals.

The present invention provides a method for producing nateglinide A-type crystals, which comprises dissolving nateglinide in a solvent in which nateglinide is highly soluble and then adding another solvent in which nateglinide is difficultly soluble or, alternatively, dissolving nateglinide in a mixed solvent composed of a solvent in which nateglinide is highly soluble and another solvent in which it is difficultly soluble, cooling the nateglinide solution to form crystals, filtering the mixture and drying the obtained crystals at 30° C. to 80° C.

The present invention also provides a method for producing nateglinide M-type crystals, which comprises dissolving nateglinide in a solvent in which nateglinide is highly soluble, adding another solvent in which nateglinide is difficultly soluble to the resultant solution, and drying the obtained product in the form of a gel at a temperature of 5° C. to below 30° C.

The present invention also provides a method for producing nateglinide P-type crystals, which comprises dissolving nateglinide in a mixed solvent composed of a solvent in which nateglinide is highly soluble and another solvent in which it is difficultly soluble, adding the same solvent in which nateglinide is difficultly soluble or another solvent in which nateglinide is difficultly soluble to the obtained nateglinide solution and isolating the obtained crystals.

The present invention also provides a method for producing nateglinide B-type crystals, which comprises treating at least one sort of crystals selected from nateglinide A-type and P-type crystals at a temperature of 60° C. or above.

The present invention also provides a method for producing nateglinide B-type crystals, which comprises treating nateglinide M-type crystals at 40° C. to below 100° C. at an RH of 60% to 95%.

BEST MODE FOR CARRYING OUT THE INVENTION

Nateglinide used for producing nateglinide A-type, M-type and P-type crystals in the present invention is available by methods disclosed in Japanese Patent Publication No. Hei 4-15221 and Japanese Patent No. 2,508,949. The crystal type of nateglinide may be either B-type or H-type. The form of nateglinide is not particularly limited, and it may be in the form of a solvate or amorphous powder thereof. The solvates are, for example, hydrates, solvates with methanol and solvates with ethanol. The amorphous powders are, for example, those obtained when the solvates lose their crystal forms by drying or the like. Nateglinide A-type, M-type and P-type crystals of the present invention may be used as the starting materials for obtaining the intended crystal forms.

Figure 1:
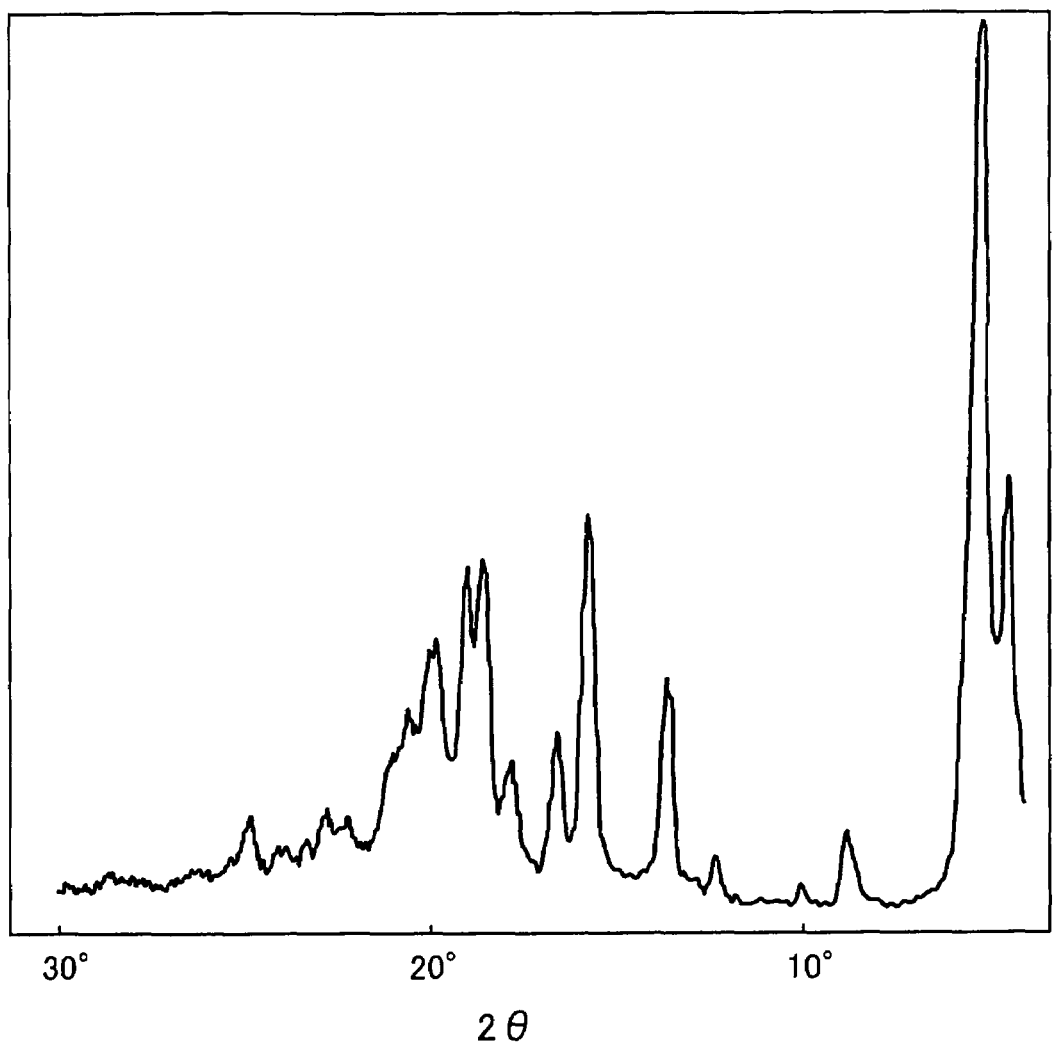
FIG. 1 shows a powder X-ray diffraction pattern of nateglinide A-type crystals.
Figure 2:
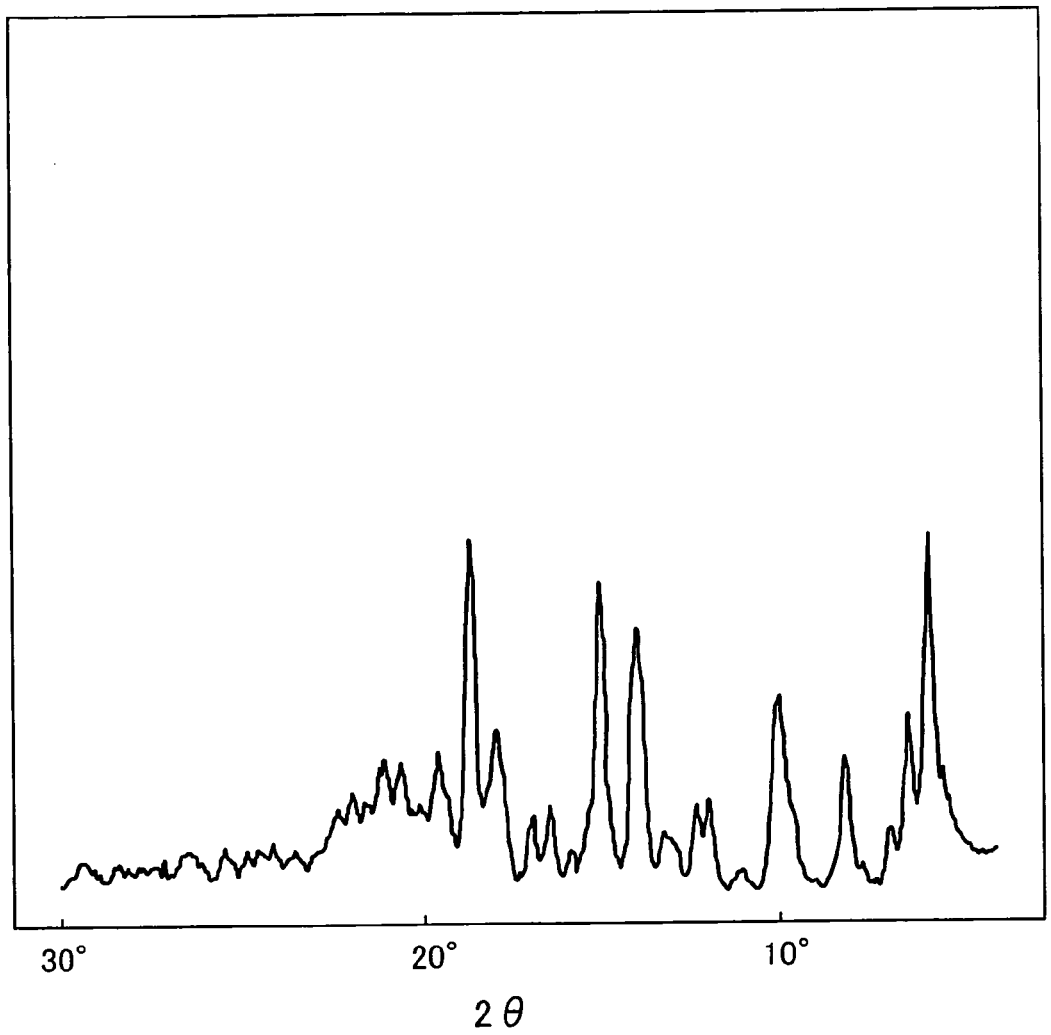
FIG. 2 shows a powder X-ray diffraction pattern of nateglinide M-type crystals.
Figure 3:
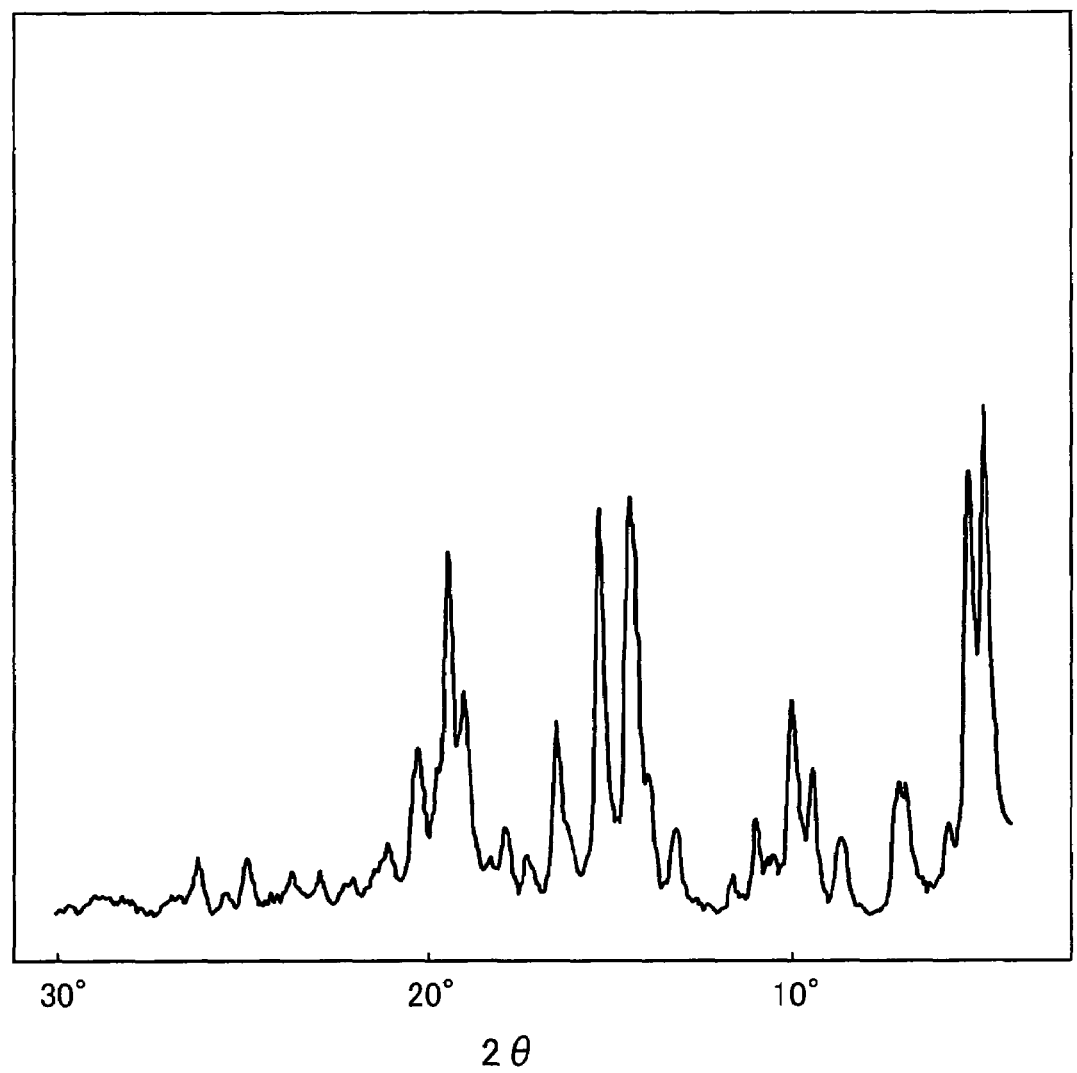
FIG. 3 shows a powder X-ray diffraction pattern of nateglinide P-type crystals.

The powder X-ray diffraction patterns of nateglinide A-type, M-type and P-type crystals of the present invention are shown in FIGS. 1 to 3.

The main peaks in the powder X-ray diffraction patterns of nateglinide A-type, M-type and P-type crystals of the present invention are as follows:

A-type crystals: 4.4°, 5.2°, 15.7°, 18.5° (2θ)
M-type crystals: 6.0°, 14.2°, 15.2°, 18.8° (2θ)
P-type crystals: 4.8°, 5.3°, 14.3°, 15.2° (2θ)

The main peaks in DSC (differential scanning calorimetry) of nateglinide A-type, M-type and P-type crystals of the present invention are as follows:

| A-type crystals: | 130 | (° C.) |
| M-type crystals: | 120, 126, 128, 137 | (° C.) |
| P-type crystals: | 95, 100, 130 | (° C.) |

The nateglinide A-type, M-type and P-type crystals of the present invention can be produced as described below. In the present invention, the solvents in which nateglinide is highly soluble are those in which at least 1% by weight of nateglinide is soluble at 30° C. The solvents are, for example, alcohols such as methanol, ethanol and isopropanol, acetone, tetrahydrofuran and dioxane. The solvents in which nateglinide is difficultly soluble are those in which less than 0.01% by weight of nateglinide is soluble at 30° C. The solvents are, for example, water, hexane and diethyl ether.

A-type crystals can be produced by dissolving nateglinide in a solvent in which nateglinide is highly soluble, then adding a solvent in which nateglinide is difficultly soluble and leaving the obtained mixture to stand to form crystals or, alternatively, by dissolving nateglinide in a mixed solvent composed of a solvent in which nateglinide is highly soluble and another solvent in which it is difficultly soluble, cooling the nateglinide solution to form crystals, filtering the mixture and drying the obtained crystals at 30° C. to 80° C.

The solvents usable for forming crystals by dissolving nateglinide in a solvent in which nateglinide is highly soluble, then adding a solvent in which nateglinide is difficulty soluble and leaving the obtained mixture to stand to form crystals may be one of those described above. The solvents in which nateglinide is highly soluble are preferably ethanol, dioxane and acetone, and the solvent in which nateglinide is difficultly soluble is preferably water. In this case, it is preferred to add 1 to 100 parts by weight of the solvent in which nateglinide is difficultly soluble to 100 parts by weight of the solvent in which nateglinide is highly soluble. Nateglinide is desirably dissolved in the solvent, in which it is highly soluble, at a temperature of 0 to 40° C. After the addition of the solvent in which nateglinide is difficultly soluble, the obtained mixture is desirably left to stand at −10 to 30° C.

The mixed solvent is preferably ethanol/water. In particular, an aqueous ethanol solution having an ethanol content of 1 to 99% by weight is preferred. Nateglinide may be dissolved in the mixed solvent at room temperature or under heating. After the dissolution, the cooling temperature for forming the crystals must be lower than 10° C. Preferably, the reaction mixture is cooled to, for example, 5° C. by ice water. The crystals separated by the filtration may be dried at a temperature described above, preferably 40 to 60° C. The crystals may be dried under reduced pressure in this step.

Nateglinide M-type crystals can be produced by dissolving nateglinide in a solvent in which nateglinide is highly soluble, adding a solvent in which nateglinide is difficultly soluble to the resultant solution, and drying the obtained product in the form of a gel at a temperature of 5° C. to below 30° C. In this case, it is preferred to add 1 to 1000 parts by weight of the solvent in which nateglinide is difficultly soluble to 100 parts by weight of the solvent in which nateglinide is highly soluble. Nateglinide is desirably dissolved in the solvent, in which it is highly soluble, at a temperature of 10 to 40° C.

The solvents usable for forming crystals by dissolving nateglinide in a solvent in which nateglinide is highly soluble, then adding a solvent in which nateglinide is difficultly soluble and leaving the obtained mixture to stand to form crystals may be those described above like the case of producing the A-type crystals. A preferred solvent in which nateglinide is highly soluble is dichloromethane and that in which nateglinide is difficultly soluble is hexane. The product in the form of a gel can be dried at a temperature described above, preferably at 20° C. to 25° C. The product can be dried under reduced pressure.

P-type crystals can be produced by dissolving nateglinide in a mixed solvent composed of a solvent in which nateglinide is highly soluble and another solvent in which it is difficultly soluble, adding the same solvent in which nateglinide is difficultly soluble or another solvent in which nateglinide is difficultly soluble to the obtained nateglinide solution, filtering the obtained crystals and drying them at a temperature of 5° C. to below 30° C.

The mixed solvent usable herein is a combination of the above-described solvents like in the production of A-type crystals. In this case, it is preferred to use a mixed solvent obtained by adding 10 to 500 parts by weight of the solvent in which nateglinide is difficultly soluble to 100 parts by weight of the solvent in which nateglinide is highly soluble. The solvent in which nateglinide is difficultly soluble and which is to be added to the mixed solvent is preferably used in such that an amount of the solvent in the mixed solvent obtained after the addition thereof will be 20 to 80% by weight.

A preferred example of the mixed solvent of a solvent in which nateglinide is highly soluble and a solvent in which nateglinide is difficultly soluble is ethanol/water. The aqueous solution having an ethanol content of 20 to 80% by weight is particularly preferred. The solvent in which nateglinide is difficultly soluble and which is to be added after the dissolution is preferably hexane or water. The obtained crystals are dried at the above-described temperature, preferably 20° C. to 25° C. The product can be dried under reduced pressure.

A-type crystals, M-type crystals or P-type crystals can be effectively produced by adding seed crystals for the intended crystals in the course of the production. The drying time can be suitably controlled depending on the solvent content of the crystals obtained after the filtration.

Nateglinide B-type crystals can be produced by drying at least one of A-type and P-type crystals, produced by the above-described methods, at 60° C. or above. The crystals may be dried under reduced pressure. The drying temperature is 60° C. or above, preferably 70° C. or above and more preferably 80° C. or above. The upper limit of the drying temperature is preferably 100° C.

The nateglinide B-type crystals can be produced by drying M-type crystals at a temperature of 40° C. to below 100° C. at an RH of 60% to 95%.

In all the processes for producing any crystal form of nateglinide by dissolving nateglinide, the concentration of nateglinide is preferably 0.1 to 20% by weight, more preferably 1 to 10% by weight. The crystals thus formed can be separated from the solvent by an optimum method, which varies depending on the scale, such as filtration or centrifugal separation.

The following Examples will further illustrate the present invention.

REFERENTIAL EXAMPLE 1

Production of B-Type Crystals 60 ml of ethanol (concentration: 97% by weight) and 40 ml of water were added to 5 g of nateglinide H-type crystals to dissolve the crystals at 30° C. The obtained solution was slowly cooled to 5° C. under stirring. The crystals thus formed were taken by the filtration and then dried at 90° C. under reduced pressure overnight to obtain B-type crystals.

EXAMPLE 1

Production of A-Type Crystals 5 g of nateglinide H-type crystals were added to 95 g of ethanol/water (60/40 v/v) mixed solvent and they were stirred at room temperature to obtain a solution. The solution was cooled at a rate of 5° C./hr to 5° C. to form crystals. The crystals were filtered and then dried at 45° C. under reduced pressure for 8 hours to obtain A-type crystals.

EXAMPLE 2

Production of M-Type Crystals 1.5 ml of methylene chloride was added to 0.3 g of nateglinide H-type crystals and they were stirred at room temperature to obtain a solution. 6.2 ml of hexane was added to the solution and then the obtained substance in the form of a gel was dried at room temperature under reduced pressure for 12 hours to obtain the M-type crystals.

EXAMPLE 3

Production of P-Type Crystals 50 ml of ethanol and 50 ml of water were added to 4 g of nateglinide H-type crystals, and they were heated to 47° C. to obtain a solution. 25 ml of water previously heated to 53° C. was added to the solution during 50 minutes. The crystals thus formed were aged by stirring the mixture at 40° C. for 12 hours and then filtered to obtain P-type crystals.

EXAMPLE 4

Production of B-Type Crystals from A-Type and P-Type Crystals

Each of Nateglinide A-type crystals and P-type crystals was dried at 90° C. under reduced pressure for 3 hours. The results of the powder X-rays of the obtained crystals coincided with those of the B-type crystals.

EXAMPLE 5

Production of B-Type Crystals from M-Type Crystals

Nateglinide M-type crystals were left to stand under heating under humid conditions (60° C., 85% RH) for 20 days. Thereafter, the results of the powder X-ray of the crystals coincided with those of B-type crystals.

The nateglinide A-type, M-type and P-type crystals of the present invention are industrially useful because they can be easily converted to useful B-type crystals.

What is claimed is:

1. Nateglinide A-type crystals having the following powder X-ray diffraction peaks: 4.4°, 5.2°, 15.7°, 18.5°(2θ).

2. A method for producing nateglinide A-type crystals, which comprises dissolving nateglinide in a mixed solvent composed of a solvent in which nateglinide is highly soluble and another solvent in which it is difficultly soluble at room temperature or with heating, cooling the nateglinide solution to a temperature of below 10° C. to form crystals, filtering the mixture and drying the obtained crystals at 30° C. to 80° C.

3. The method according to claim 2 wherein the solvent in which nateglinide is highly soluble is ethanol, dioxane or acetone, and the solvent in which nateglinide is difficultly soluble is water.

4. The method according to claim 2 wherein nateglinide is dissolved in a mixed solvent of ethanol/water.

5. The method according to claim 4 wherein the drying temperature is 40 to 60° C.

6. A method for producing nateglinide B-type crystals of claim 1, which comprises treating nateglinide A-type crystals at a temperature of at least 60° C.

7. The method according to claim 6 wherein the drying temperature is 70° C. or above.

8. The method according to claim 6 wherein the drying temperature is 80° C. or above.

9. The method according to claim 6 wherein the crystals are dried under reduced pressure.

10. The method according to claim 2 wherein nateglinide is dissolved in a mixed solvent comprising ethanol and the ethanol content ranges from 1 to 99% by weight.

11. The method according to claim 2 wherein nateglinide is dissolved in a mixed solvent comprising ethanol and the ethanol content ranges from 60 to 99% by weight.

12. The method according to claim 2 wherein nateglinide is dissolved in a mixed solvent comprising ethanol and the ethanol content ranges from 1 to 60% by weight.

13. The method according to claim 2 wherein said drying is under reduced pressure.

14. The method according to claim 2 wherein the concentration of nateglinide ranges from 0.1 to 20% by weight.

15. The method according to claim 2 wherein the concentration of nateglinide ranges from 1 to 10% by weight.

* * * * *